(12) United States Patent
Atamna

(10) Patent No.: US 7,906,499 B2
(45) Date of Patent: Mar. 15, 2011

(54) POLYCARBOXYLATED PORPHYRINS AND USE THEREOF IN TREATMENT OF METAL TOXICITIES

(75) Inventor: Hani Atamna, Berkeley, CA (US)

(73) Assignee: Children's Hospital & Research Center at Oakland, Oakland, CA (US)

( * ) Notice: Subject to any disclaimer, the term of this patent is extended or adjusted under 35 U.S.C. 154(b) by 712 days.

(21) Appl. No.: 11/046,415

(22) Filed: Jan. 29, 2005

(65) Prior Publication Data

US 2006/0172986 A1 Aug. 3, 2006

(51) Int. Cl.
| | |
|---|---|
| *A01N 43/00* | (2006.01) |
| *A01N 43/38* | (2006.01) |
| *A61K 31/33* | (2006.01) |
| *A61K 31/40* | (2006.01) |
| *C09B 62/00* | (2006.01) |
| *C09B 47/04* | (2006.01) |
| *C09B 67/00* | (2006.01) |
| *C09B 47/00* | (2006.01) |
| *C07D 487/22* | (2006.01) |

(52) U.S. Cl. ......... 514/183; 514/410; 540/122; 540/145
(58) Field of Classification Search .................. 514/183, 514/410; 540/122, 145
See application file for complete search history.

(56) References Cited

U.S. PATENT DOCUMENTS

| | | | | | |
|---|---|---|---|---|---|
| 4,236,892 | A | * | 12/1980 | Duron et al. ..................... | 436/98 |
| 5,354,652 | A | * | 10/1994 | Silbergeld ......................... | 435/4 |
| 5,935,790 | A | * | 8/1999 | Poretz et al. ...................... | 435/6 |
| 5,955,490 | A | * | 9/1999 | Kennedy et al. ............... | 514/410 |
| 6,365,414 | B1 | * | 4/2002 | Tanzi et al. ..................... | 436/86 |
| 2002/0115223 | A1 | * | 8/2002 | Tanzi et al. ..................... | 436/86 |
| 2002/0187959 | A1 | * | 12/2002 | Eliaz .............................. | 514/54 |
| 2003/0004204 | A1 | * | 1/2003 | Sakalosky ..................... | 514/410 |
| 2003/0235531 | A1 | * | 12/2003 | Adair ........................... | 424/1.11 |
| 2005/0089972 | A1 | * | 4/2005 | Schmidt-Dannert et al. . | 435/106 |
| 2005/0101565 | A1 | * | 5/2005 | Dasseux ........................ | 514/58 |

OTHER PUBLICATIONS

Maha F. Tutunji et al., Disappearance of heme metabolites following chelation therapy with meso 2,3-dimercaptosuccinic acid, 1994, Clinical Toxicology, 32(3), 267-276.*

Harris et al., Enhancement of bacterial porphyrin biosynthesis by exogenous aminolevulinic acid and isomer specificity of the products, 1993, Bioorganic chemistry, 21, 209-220.*

Lascelles, The synthesis of exzymes concerned in bacteriochlorophyll formation in growing cultures of *Rhodopseudomonas spheroides*, 1060, J. gen. Microbiol., 23, 487-498.*

* cited by examiner

*Primary Examiner* — Johann R Richter
*Assistant Examiner* — Luke E Karpinski
(74) *Attorney, Agent, or Firm* — Richard Aron Osman

(57) ABSTRACT

Metal binding polycarboxylated porphyrins, their precursors, or cofactors in the porphyrin biosynthetic pathway, are administered to individuals determined to be subject to or predisposed to a polycarboxylated porphyrin-binding metal toxicity to increase the level of the metal-binding polycarboxylated porphyrin in the individual.

20 Claims, No Drawings

POLYCARBOXYLATED PORPHYRINS AND USE THEREOF IN TREATMENT OF METAL TOXICITIES

BACKGROUND OF THE INVENTION

Biosynthesis of the tetrapyrrole (porphyrin) ring of heme (protoporphyrin IX) starts in the mitochondrial matrix. Succinyl-CoA donated from the Krebs cycle in the mitochondria condenses with glycine from the mitochondrial pool of this amino acid to form δ-aminolevulinic acid (ALA). ALA is then exported to the cytoplasm where the enzyme δ-aminolevulinic acid dehydratase (ALAD), also called porphobilinogen (PBG) synthase, condenses two molecules of ALA to form porphobilinogen. Next, a tetrapyrrole is formed through the enzymatic action of porphobilinogen deaminase and the condensation of four molecules of PBG. Uroporphyrinogen III synthase catalyzes ring closure, converting the linear tetrapyrrole, hydroxymethylbilane, to uroporphyrinogen III, the first in a series of porphyrin intermediates that are produced by decarboxylation and oxidation reactions. Only a small fraction of the porphyrin intermediates return to the mitochondria and provide protoporphyrin IX, the precursor for heme. The rest of the porphyrins are excreted, without any apparent function.

All tissue types synthesize porphyrins and heme, although their capacities for regulation and such biosynthesis vary. The micronutrient requirements, however, of all tissues for the production of heme and porphyrins as well as the known inhibitors and inducers are identical. Heme biosynthesis in the brain, for example, varies according to the type of brain cell. Heme biosynthesis appears to be higher in non-neuronal cells and lower in neuronal cells (Whetsell, 1978). Heme and porphyrin metabolism are disturbed in Alzheimer disease (Atamna, 2004) or after exposure to environmental toxins including metals (Daniell, 1997). The mechanisms underlying these disturbances are not known, but porphyrin intermediates are excessively produced. We have previously observed that heme and heme-α deficiencies, which were induced in human cells in vitro, and in primary hippocampal neurons from rats, induced cytological changes that mimicked the cytopathology of the brain during AD (Atamna, 2002).

The Krebs cycle is an amphibolic pathway; the intermediates of the Krebs cycle supply or receive the carbon skeleton of several metabolites in anabolic and catabolic processes. The intermediates of the Krebs cycle are the precursors for several anabolic processes, including the biosynthesis of porphyrins, amino acids, purines, pyrimidines, fatty acids, sterols, and some neurotransmitters. These metabolites, except for the porphyrins, provide the Krebs cycle with the intermediates when they are turned over by the metabolic activity of the cell. Some of these metabolites such as the amino acids and fatty acids are consumed in the diet; porphyrins and heme are not bio-available from the diet and must be synthesized in situ. Therefore, in most of these metabolic activities, the Krebs cycle reclaims the complete or partial intermediates by salvage or through a recycling mechanism.

No biological function has been ascribed for the porphyrins, other than as a precursor for heme. Unlike the recycled Krebs intermediates, porphyrins are continuously excreted from the body. Porphyrins usually leave the body in two ways: 1) continuously excreted directly in the urine and 2) excreted as bile pigment when heme is turned over to bilirubin. Therefore a net efflux of succinyl-CoA from Krebs cycle occurs as porphyrins are synthesized.

The biosynthesis of one mole of heme requires 8 moles of succinyl-CoA (Ponka, 1999; Woods, 1976) from the Krebs cycle and 8 moles of glycine from the mitochondrial pool of amino acids. Because not all the porphyrin produced by the heme biosynthetic pathway becomes heme (some porphyrin side products are excreted), the quantity of succinyl-CoA that consumed from the TCA cycle for porphyrin biosynthesis exceeds 8 moles/1 mol heme. It is well known that the porphyrin synthetic pathway produces a mixture of porphyrin side products (e.g. uroporphyrin I & III, coproporphyrin I & III) (Ponka, 1999). In rodents (F-344), about 2 nmols/day (Bowers, 1992) of total porphyrins are excreted in urine; this figure increases 100-1000 fold in humans (Daniell, 1997). Only 5% of these porphyrins are converted to heme, as demonstrated in rat primary olfactory receptor neurons (Ingi, 1996). In addition, it is estimated that between 20 and 35% of newly formed heme is directly converted to bile pigments (Grandchamp, 1981), suggesting a continuous demand for heme biosynthesis. Therefore, it appears that the synthetic pathway of porphyrins is energy consuming and drains much succinyl-CoA from the Krebs cycle.

We now show that the changes in the biosynthesis of porphyrin and heme in Alzheimer's disease are a response to the pathological conditions of the brain and that porphyrins can be used in prevention and treatment of AD and other metal-related disorders.

OTHER RELEVANT REFERENCES

Caughey and Caughey (2003), Priola et al, (2000), and Caughey et al. (1998) disclose administration of tetrapyrroles, including porphyrins, to inhibit progression of an amyloidogenic disease.

Howlett et al. (1997) disclose inhibition of β-amyloid aggregation in vitro by hemin, hematin, and zinc protoporphyrin IX.

Miller et al. (2002) disclose that low vitamin B6 status is prevalent in patients with Alzheimer's disease.

Brown et al. (2004) and Gold et al (2004) disclose δ-aminolevulinic acid for photodynamic tumor therapy.

SUMMARY OF THE INVENTION

One aspect of the invention is a method for increasing an amount of a metal-binding, polycarboxylated porphyrin in an individual, the method comprising: (a) determining that the individual is subject to or predisposed to a polycarboxylated porphyrin-binding metal toxicity; (b) increasing the level of the metal-binding polycarboxylated porphyrin in the individual by administering the porphyrin, wherein the porphyrin has a tetrapyrrole structure I:

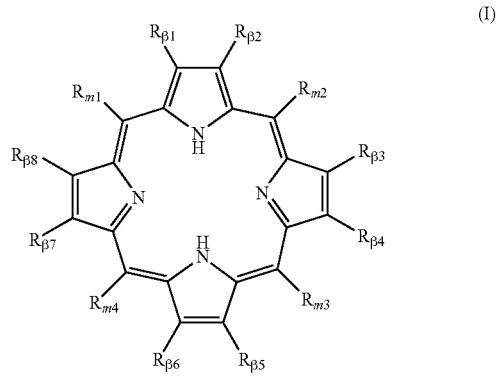

wherein the eight $R_\beta$ positions and the four $R_m$ positions are independently H, lower alkyl, lower alkyloxyl, or lower alkylcarboxyl, wherein at least one $R_\beta$ position at each pyrrole is lower alkylcarboxyl, wherein the lower alkyl is C1-C4; and (c) detecting a resultant increase in the amount of the metal-binding, polycarboxylated porphyrin in the individual.

In one embodiment of the invention, $R_{\beta 1}$, $R_{\beta 3}$, $R_{\beta 5}$ and $R_{\beta 8}$ are methylcarboxyl, and $R_{\beta 2}$, $R_{\beta 4}$, $R_{\beta 6}$ and $R_{\beta 7}$ are ethylcarboxyl. In a further embodiment, the porphyrin is uroporphyrin III.

In another embodiment, $R_{\beta 1}$, $R_{\beta 3}$, $R_{\beta 5}$ and $R_{\beta 7}$ are methylcarboxyl, and $R_{\beta 2}$, $R_{\beta 4}$, $R_{\beta 6}$ and $R_{\beta 8}$ are ethylcarboxyl. In a further embodiment, the porphyrin is uroporphyrin I.

In one embodiment, $R_{\beta 1}$, $R_{\beta 3}$, $R_{\beta 5}$ and $R_{\beta 8}$ are methyl, and $R_{\beta 2}$, $R_{\beta 4}$, $R_{\beta 6}$ and $R_{\beta 7}$ are ethylcarboxyl. In a further embodiment, the porphyrin is coproporphyrin III.

In one embodiment, $R_{\beta 1}$, $R_{\beta 3}$, $R_{\beta 5}$ and $R_{\beta 7}$ are methyl, and $R_{\beta 2}$, $R_{\beta 4}$, $R_{\beta 6}$ and $R_{\beta 8}$ are ethylcarboxyl. In a further embodiment, the porphyrin is coproporphyrin I.

In one embodiment of the invention, the metal is selected from the group consisting of $Al^{+++}$, $Hg^{++}$, $Cd^{+++}$, $Cu^+$, $Mn^+$, and $Zn^{++}$.

In one embodiment of the invention, the determining step comprises determining that the individual is subject to or predisposed to amyloid-β (Aβ) aggregation.

Another aspect of the invention is a method for increasing an amount of a metal-binding, polycarboxylated human porphyrin in an individual, the method comprising: (a) determining that the individual is subject to or predisposed to a polycarboxylated porphyrin-binding metal toxicity; (b) increasing the level of the metal-binding polycarboxylated human porphyrin in the individual by administering the porphyrin or a precursor of the porphyrin, wherein the porphyrin is selected from the group consisting of uroporphyrin I, uroporphyrin III, coproporphyrin I, and coproporphyrin III; and (c) detecting a resultant increase in the amount of the metal-binding, polycarboxylated porphyrin in the individual.

In one embodiment, in the increasing step, a porphyrin selected from the group consisting of uroporphyrin I, uroporphyrin III, coproporphyrin I, and coproporphyrin III is administered to the individual.

In another embodiment, in the increasing step, a precursor selected from the group consisting of δ-aminolevulinic acid, porphobilinogen, and hydroxymethylbilane is administered to the individual.

Another aspect of the invention is a method for increasing an amount of a metal-binding, polycarboxylated human porphyrin in an individual, the method comprising: (a) determining that the individual is subject to or predisposed to a polycarboxylated porphyrin-binding metal toxicity; and is subject to or predisposed to an associated endogenous porphyrin underproduction; (b) increasing the level of the metal-binding polycarboxylated human porphyrin in the individual by administering the porphyrin or a precursor or a cofactor in the biosynthetic pathway of the porphyrin, wherein the porphyrin is selected from the group consisting of uroporphyrin I, uroporphyrin III, coproporphyrin I, and coproporphyrin III; and (c) detecting a resultant increase in the amount of the metal-binding, polycarboxylated porphyrin in the individual.

In one embodiment, in the increasing step, a porphyrin selected from the group consisting of uroporphyrin I, uroporphyrin III, coproporphyrin I, and coproporphyrin III is administered to the individual.

In another embodiment, in the increasing step, a precursor selected from the group consisting of δ-aminolevulinic acid, porphobilinogen, and hydroxymethylbilane is administered to the individual.

In another embodiment, in the increasing step, a cofactor selected from the group consisting of pantothenic acid (vitamin B5), pyridoxal phosphate (vitamin B6), zinc, and biotin (vitamin H) is administered to the individual.

Another aspect of the invention is a method for prescribing an individual with porphyrin enhancement therapy, the method comprising: (a) determining an individual is subject to or predisposed to a polycarboxylated human porphyrin-binding metal toxicity, (b) determining the individual is subject to or predisposed to an associated endogenous porphyrin underproduction, and (c) prescribing the individual with a treatment protocol that comprises administration of the porphyrin, or a precursor or cofactor in the biosynthetic pathway of the porphyrin, to effect enhancement of porphyrin production in the individual, wherein the porphyrin is selected from the group consisting of uroporphyrin I, uroporphyrin III, coproporphyrin I, and coproporphyrin III.

In one embodiment, the method further comprises: (d) detecting a resultant enhancement of endogenous porphyrin production in the individual.

Another aspect of the invention is a pharmaceutical composition comprising a pharmaceutically acceptable metal-binding, polycarboxylated porphyrin in unit dosage and a pharmaceutically acceptable excipient, wherein the porphyrin has a tetrapyrrole structure I, wherein the eight $R_\beta$ positions and the four $R_m$ positions are independently H, lower alkyl, lower alkyloxyl, or lower alkylcarboxyl, wherein at least one $R_\beta$ position at each pyrrole is lower alkylcarboxyl, wherein the lower alkyl is C1-C4.

In one embodiment, $R_{\beta 1}$, $R_{\beta 3}$, $R_{\beta 5}$ and $R_{\beta 8}$ are methylcarboxyl, and $R_{\beta 2}$, $R_{\beta 4}$, $R_{\beta 6}$ and $R_{\beta 7}$ are ethylcarboxyl.

In another embodiment, $R_{\beta 1}$, $R_{\beta 3}$, $R_{\beta 5}$ and $R_{\beta 7}$ are methylcarboxyl, and $R_{\beta 2}$, $R_{\beta 4}$, $R_{\beta 6}$ and $R_{\beta 8}$ are ethylcarboxyl.

In another embodiment, $R_{\beta 1}$, $R_{\beta 3}$, $R_{\beta 5}$, and $R_{\beta 8}$ are methyl, and $R_{\beta 2}$, $R_{\beta 4}$, $R_{\beta 6}$ and $R_{\beta 7}$ are ethylcarboxyl.

In another embodiment, $R_{\beta 1}$, $R_{\beta 3}$, $R_{\beta 5}$ and $R_{\beta 7}$ are methyl, and $R_{\beta 2}$, $R_{\beta 4}$, $R_{\beta 6}$ and $R_{\beta 8}$ are ethylcarboxyl.

In a further embodiment, the porphyrin is a human porphyrin selected from the group consisting of uroporphyrin I, uroporphyrin III, coproporphyrin I, and coproporphyrin III.

In a further embodiment, the pharmaceutical composition is copackaged with instructional material reciting a method for using the composition to increase polycarboxylated porphyrin levels in an individual subject to or predisposed to a polycarboxylated porphyrin-binding metal toxicity.

Another aspect of the invention is a pharmaceutical composition comprising an active agent selected from the group consisting of δ-aminolevulinic acid, porphobilinogen, hydroxymethylbilane, pantothenic acid (vitamin B5), pyridoxal phosphate (vitamin B6), zinc, and biotin (vitamin H) in unit dosage and a pharmaceutically acceptable excipient, copackaged with instructional material reciting a method for using the composition to increase polycarboxylated porphyrin levels in an individual subject to or predisposed to a polycarboxylated porphyrin-binding metal toxicity.

Another aspect of the invention is a method for marketing a pharmaceutical composition comprising an active agent selected from the group consisting of δ-aminolevulinic acid, porphobilinogen, hydroxymethylbilane, pantothenic acid (vitamin B5), pyridoxal phosphate (vitamin B6), zinc, and biotin (vitamin H), said method comprising promoting use of the composition by an individual determined to be subject to or predisposed to a polycarboxylated porphyrin-binding metal toxicity.

DETAILED DESCRIPTION OF SPECIFIC EMBODIMENTS OF THE INVENTION

The invention provides a method for increasing an amount of a metal-binding, polycarboxylated porphyrin in an individual comprising (a) determining that the individual is subject to or predisposed to a polycarboxylated porphyrin-binding metal toxicity; (b) increasing the level of the metal-binding polycarboxylated porphyrin in the individual; and (c) detecting a resultant increase in the amount of the metal-binding, polycarboxylated porphyrin in the individual.

The polycarboxylated porphyrins of the invention have a tetrapyrrole structure I:

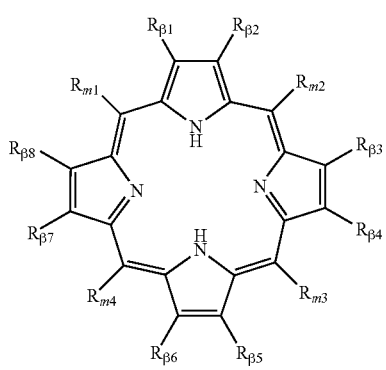

wherein the eight $R_\beta$ positions and the four $R_m$ positions are independently H, lower alkyl, lower alkyloxyl, or lower alkylcarboxyl, wherein at least one $R_\beta$ position at each pyrrole is lower alkylcarboxyl, wherein the lower alkyl is C1-C4.

In one embodiment of the invention, $R_{\beta 1}$, $R_{\beta 3}$, $R_{\beta 5}$ and $R_{\beta 8}$ are methylcarboxyl, and $R_{\beta 2}$, $R_{\beta 4}$, $R_{\beta 6}$ and $R_{\beta 7}$ are ethylcarboxyl. In another embodiment, $R_{\beta 1}$, $R_{\beta 3}$, $R_{\beta 5}$, and $R_{\beta 7}$ are methylcarboxyl, and $R_{\beta 2}$, $R_{\beta 4}$, $R_{\beta 6}$ and $R_{\beta 8}$ are ethylcarboxyl In another embodiment, $R_{\beta 1}$, $R_{\beta 3}$, $R_{\beta 5}$ and $R_{\beta 8}$ are methyl, and $R_{\beta 2}$, $R_{\beta 4}$, $R_{\beta 6}$ and $R_{\beta 7}$ are ethylcarboxyl. In another embodiment, $R_{\beta 1}$, $R_{\beta 3}$, $R_{\beta 5}$ and $R_{\beta 7}$ are methyl, and $R_{\beta 2}$, $R_{\beta 4}$, $R_{\beta 6}$ and $R_{\beta 8}$ are ethylcarboxyl.

In one embodiment of the invention, the polycarboxylated porphyrin is a human porphyrin, having the same structure as an endogenously produced porphyrin. In one embodiment, the human porphyrin is an intermediate of the heme biosynthetic pathway and is selected from the group consisting of uroporphyrin I, uroporphyrin III, coproporphyrin I, and coproporphyrin III.

In the determining step, the individual is identified as subject to or predisposed to a polycarboxylated porphyrin-binding metal toxicity. Polycarboxylated porphyrin-binding metal toxicities include metal toxicity from environmental exposure, and disorders characterized by disturbances in metal ion homeostasis, particularly disorders that result in metal ion accumulation. Examples of such disorders include Wilson's disease, in which copper transport is defective (e.g. Nakayama, 2000); aceruloplasminemia, an iron metabolism disorder (e.g. Miyajima, 2003); and diseases involving metal-facilitated protein aggregation such as zinc, copper, or iron facilitated-aggregation of Aβ in Alzheimer's disease (e.g. Atamna, 2004), and aluminum, copper, iron, cobalt, or manganese facilitated-aggregation of α-synuclein in Parkinson's disease (e.g. Uversky, 2001). Conventional spectroscopy assays (e.g. Beer, 2003) can be used to determine whether a given polycarboxylated porphyrin binds the toxic metal of interest (e.g. Example 2, below). In particular embodiments, the metal is selected from the group consisting of $Al^{+++}$, $Hg^{++}$, $Cd^{+++}$, $Cu^+$, $Mn^+$, and $Zn^{++}$.

Determining whether the individual is subject to or predisposed to a polycarboxylated porphyrin-binding metal toxicity may be effected by a variety of established techniques, both directly and inferentially, depending on what is presumed to be the underlining toxicity or disorder. Metal toxicity in an individual can be routinely tested by measuring metal content in a biological sample, such as hair, urine and/or blood (e.g. Mehra, 2003). In one embodiment, the determining step comprises determining that the individual is subject to or predisposed to Aβ aggregation. Conventional diagnostic markers may be utilized in the determination, such as the cerebrospinal fluid biomarkers total-tau, phospho-tau, and the 42 amino acid form of beta-amyloid. Brain scans may also be used to assist in diagnosing AD aggregation in individuals suspected of having Alzheimer's disease (e.g. Lee, 2004; Lerch 2004). Alpha synuclein may be detected in patient samples in the diagnosis of Parkinson's disease (e.g. Al-Agnaf, 2003). Changes in the metabolism of porphyrins can also be used as markers to identify individuals with predisposition to a polycarboxylated porphyrin-binding metal toxicity, such as Alzheimer's disease, or to assess the clinical status of individuals diagnosed with a polycarboxylated porphyrin-binding metal toxicity. Quantitative porphyrin analyses routinely available at clinical laboratories can be used to determine levels of endogenous porphyrins. In some cases, the individual may have been previously diagnosed with a polycarboxylated porphyrin-binding metal toxicity, and the determining step comprises a review of the individual's medical history, such as examination of medical records, determination of family history, and/or a review of laboratory test results. In other cases, predisposition to a polycarboxylated porphyrin-binding metal toxicity may be determined based on genetic information, family history, known environmental exposure, etc., depending on the particular toxicity or disorder in question. For example, a determination that an individual is homozygous for the ApoE4 variant of apolipoprotein E may be used to determine a predisposition to Alzheimer's Disease.

In preferred embodiments, the individual is a human, but can also be any mammal in which treatment of a polycarboxylated porphyrin-binding metal toxicity is desired, such as pets and livestocks. The individual may also be an animal model of a polycarboxylated porphyrin-binding metal toxicity.

In the increasing step, according to one embodiment of the invention, the level of metal-binding polycarboxylated porphyrin in the individual is increased by administering the polycarboxylated porphyrin to the individual. Polycarboxylated porphyrins are commercially available (e.g. Frontier Scientific, Logan Utah). Methods and compositions for administering porphryins pharmaceutically are known in the art (e.g. Caughey, 2003) and include oral, inhalation, subcutaneous, intracranial ventricular, intrathecal, intravenous, and intramuscular administration methods. Optimal dosage regimes and administration protocols for particular porphyrins can be determined from established work with other known chelating agents such as clioquinol (e.g. Ritchie, 2004), dimercaprol, and EDTA, and empirically.

In the detecting step, the resultant increase in the amount of the metal-binding, polycarboxylated porphyrin in the individual may be directly measured, such as by routine porphyrin level testing. Alternatively, the resultant increase may be inferred from the amelioration of symptoms of the metal toxicity, reduced levels of metal in the blood, etc. The detecting may be used to monitor progress or effectiveness of the treatment, and can be carried at various time points during and/or after treatment.

In another aspect of the invention, the polycarboxylated porphyrin is a human porphyrin, and the increasing step comprises administering the individual the porphyrin or a precursor of the porphyrin. A human porphyrin has the same structure as a porphyrin that is normally synthesized in humans. In one embodiment, the human porphyrin is selected from the group consisting of uroporphyrin I, uroporphryin III, coproporphyrin I, or coproporphyrin III. Human porphyrins are commercially available (e.g. Frontier Scientific, Logan Utah). Porphyrin precursors are the subunits and molecules normally utilized in the human porphyrin biosynthetic pathway and include glycine, succinyl-CoA, δ-aminolevulinic acid, porphobilinogen, and hydroxymethylbilane. In one embodiment of the invention, a porphyrin precursor is administered to the individual, wherein the precursor is selected from the group consisting of δ-aminolevulinic acid, porphobilinogen, and hydroxymethylbilane. Porphyrin precursors are commercially available (e.g. Frontier Scientific, Logan Utah). Routes of porphyrin precursor administration include oral, inhalation, subcutaneous, intracranial ventricular, intrathecal, intravenous, and intramuscular administration methods. Optimal dosage regimes and administration protocols for particular precursors can be determined from routine animal model studies and clinical trials.

In another aspect of the invention, the determining step additionally comprises determining that the individual is subject to or predisposed to an associated endogenous porphyrin underproduction. This determination may be made by porphyrin testing that shows reduced levels of urine or blood porphyrins. Endogenous porphyrins include uroporphyrin I, uroporphryin III, coproporphyrin I, or coproporphyrin III. Endogenous porphyrin underproduction may also be concluded from results showing defects in the porphyrin biosynthetic pathway. Additionally, inadequate nutrition and/or vitamin deficiencies may result in an individual being subject to or predisposed to an endogenous porphyrin underproduction, as can be common in elderly patients. Patients with known kidney dysfunction may also be prone to porphyrin underproduction, and testing may be warranted. In some cases, the individual may have been previously diagnosed as having endogenous porphyrin underproduction, may have a family history of defective porphyrin biosynthesis, or may have known environmental exposure to toxic metals. In these cases, the determining step may comprise a review of the individual's medical history, such as examination of medical records, determination of family history, environmental exposure, and/or a review of laboratory test results. In other cases, predisposition to an associated endogenous porphyrin underproduction may be determined by identification of a polymorphism or other genetic defect that correlates with defective porphyrin biosynthesis, and/or laboratory testing results, etc. A determination of endogenous porphyrin underproduction may also be inferred from routine blood tests showing levels of metals above normal physiologic concentrations.

In individuals identified as having an associated endogenous porphyrin underproduction, the increasing step may comprise administering the porphyrin or a precursor of the porphyrin to the individual, as described above, or may alternatively comprise administering a cofactor in the biosynthetic pathway of the human porphyrin. Cofactors in porphyrin biosynthesis include pantothenic acid (vitamin B5), a cofactor of succinyl-CoA; pyridoxal phosphate (P-5-P or vitamin B6), which is a cofactor for the reaction catalyzed by aminolevulinate (ALA) synthase in which succinyl CoA and glycine are combined to form δ-aminolevulinic acid; zinc, which is a cofactor of ALA dehydratase which combines two molecules of δ-aminolevulinic acid into porphobilinogen; and biotin (vitamin H), a cofactor required for formation of succinyl CoA. The cofactors may be administered orally, intravenously, or by any other suitable route of administration. The cofactors are administered in therapeutically safe and effective amounts sufficient to increase the level of the metal-binding polycarboxylated human porphyrin in the individual. In embodiments of the invention where in the increasing step, a precursor or cofactor is administered to the individual, the method may further comprise detecting a resultant increase of endogenous production of the human porphyrin in the individual.

Certain treatment protocols can be carried out by the individual without direct supervision by medical personnel, e.g. cofactor supplements taken orally. Thus, another aspect of the invention is a method for prescribing an individual with porphyrin enhancement therapy, the method comprising: (a) determining an individual is subject to or predisposed to a polycarboxylated human porphyrin-binding metal toxicity, (b) determining the individual is subject to or predisposed to an associated endogenous porphyrin underproduction, and (c) prescribing the individual with a treatment protocol that comprises administration of the porphyrin, or a precursor or cofactor in the biosynthetic pathway of the porphyrin, to effect enhancement of the porphyrin. The method may further comprise (d) detecting a resultant enhancement of endogenous porphyrin production in the individual at one or more time points during or after the treatment.

One aspect of the invention is a pharmaceutical composition comprising a metal-binding, polycarboxylated porphyrin in unit dosage and a pharmaceutically acceptable excipient, wherein the porphyrin has structure I, wherein the eight $R_\beta$ positions and the four $R_m$ positions are independently H, lower alkyl, lower alkyloxyl, or lower alkylcarboxyl, wherein at least one $R_\beta$ position at each pyrrole is lower alkylcarboxyl, wherein the lower alkyl is C1-C4. The composition is functionally characterized by its ability, when administered to an individual subject to or predisposed to a polycarboxylated porphyrin-binding metal toxicity, to increase the level of the metal-binding polycarboxylated porphyrin and ameliorate symptoms of the metal toxicity in the individual.

In one embodiment of the invention, $R_{\beta 1}$, $R_{\beta 3}$, $R_{\beta 5}$ and $R_{\beta 8}$ are methylcarboxyl, and $R_{\beta 2}$, $R_{\beta 4}$, $R_{\beta 6}$ and $R_{\beta 7}$ are ethylcarboxyl. In another embodiment, $R_{\beta 1}$, $R_{\beta 3}$, $R_{\beta 5}$ and $R_{\beta 7}$ are methylcarboxyl, and $R_{\beta 2}$, $R_{\beta 4}$, $R_{\beta 6}$ and $R_{\beta 8}$ are ethylcarboxyl. In another embodiment, $R_{\beta 1}$, $R_{\beta 3}$, $R_{\beta 5}$ and $R_{\beta 8}$ are methyl, and $R_{\beta 2}$, $R_{\beta 4}$, $R_{\beta 6}$ and $R_{\beta 7}$ are ethylcarboxyl. In another embodiment, $R_{\beta 1}$, $R_{\beta 3}$, $R_{\beta 5}$ and $R_{\beta 7}$ are methyl, and $R_{\beta 2}$, $R_{\beta 4}$, $R_{\beta 6}$ and $R_{\beta 8}$ are ethylcarboxyl. In further preferred embodiments, the polycarboxylated porphyrin is a human porphyrin, having the same structure as an endogenously produced porphyrin. In one embodiment, the human porphyrin is an intermediate of the heme biosynthetic pathway and is selected from the group consisting of uroporphyrin I, uroporphyrin III, coproporphyrin I, and coproporphyrin III. Polycarboxylated porphyrins are commercially available (e.g. Frontier Scientific, Logan Utah), and may be prepared in any unit dosage form together with a suitable pharmaceutical excipient suitable for the intended route of administration including oral, inhalation, subcutaneous, intracranial ventricular, intrathecal, intravenous, and intramuscular administration methods (e.g. Caughey, 2003).

Another aspect of the invention is a pharmaceutical composition comprising a metal-binding, polycarboxylated porphyrin or a precursor or cofactor in the biosynthetic pathway of the porphyrin, in unit dosage and a pharmaceutically acceptable excipient, copackaged with instructional material reciting any of the above-described methods for increasing polycarboxylated porphyrin levels in an individual subject to or predisposed to a polycarboxylated porphyrin-binding metal toxicity. The polycarboxylated porphyrins, precursors, or cofactors may be prepared in any unit dosage form together with a suitable pharmaceutical excipient suitable for the intended route of administration including oral, inhalation, subcutaneous, intracranial ventricular, intrathecal, intravenous, and intramuscular administration methods (e.g. Caughey, 2003). In one embodiment, the pharmaceutical composition comprises a porphyrin selected from the group consisting of uroporphryin I, uroporphryin III, coproporphyrin I, and coproporphyrin III. In another embodiment, the pharmaceutical composition comprises a precursor of the porphyrin selected from the group consisting of δ-aminolevulinic acid, porphobilinogen, and hydroxymethylbilane. In another embodiment, the pharmaceutical composition comprises a cofactor selected from the group consisting of pantothenic acid (vitamin B5), pyridoxal phosphate (vitamin B6), zinc, and biotin (vitamin H).

Another aspect of the invention is a method for marketing an above-described polycarboxylated porphyrin or a precursor or cofactor in the biosynthetic pathway of the porphyrin, or any of the above-described pharmaceutical compositions, said method comprising promoting use of the polycarboxylated porphyrins, precursor or cofactor, or pharmaceutical composition, for an individual determined to be subject to or predisposed to a polycarboxylated porphyrin-binding metal toxicity. Any conventional media may be used for the marketing such as product labels, package inserts, internet marketing, television commercials, newspaper and magazine articles, etc. The marketing will typically include a description of the use of the porphyrins to address a porphyrin-binding metal toxicity and potential health benefits of such use.

EXAMPLES

Two endogenous porphyrins (uroporphyrin III and coproporphyrin III), that are intermediates in the heme biosynthetic pathway, and two byproducts made from them in cells (uroporphyrin I and coproporphyrin I) are made in large amounts and excreted from cells and end up in the urine. Thus, it has been mysterious why only a small fraction of the porphyrins synthesized in the body is converted into heme. We have studied possible biological functions for these four endogenous porphyrins (Upor I & III and Cpor I & III). We found that these endogenous porphyrins do not accumulate in cells, suggesting that porphyrins are maintained in a low intracellular steady-state concentration. Additionally, porphyrins added to the growth medium of cells do not enter the cells. We conclude that porphyrins are produced by the cells and secreted into the extracellular matrix. We also found that endogenous porphyrins are excellent chelators for toxic (Al+++, Hg++, & Cd++) and physiologic (Cu+, Mn+, Zn++) metals. Our results indicate that porphyrins facilitate metal homeostasis, providing a natural response of the cells to overcome and resist metallic stress by removing toxic or excess metals even before they enter the cell.

Example 1

Human Porphyrins Dissolve Metal-Induced Aβ Aggregates $A\beta_{1-40}$ (10 ng in 200 µl) aggregation is induced by incubation (30 min, RT) with $ZnCl_2$ (25 µM in TBS, pH 7.4), $CuCl_2$ (5 µM in TBS, pH 6.8), or acidic conditions (pH 5.5, MES buffered saline). Aggregates are transferred to a 0.2µ nylon membrane by filtration using a 96-well ELIFA apparatus (Pierce). The aggregates are then washed (200 µl/well) with TBS alone, TBS containing 2 µM EDTA (control), or TBS with uroproporphyrin or coproporphyrin at varying concentrations (0.1 µM-1 mM). The membrane is fixed, probed with the anti-Aβ monoclonal antibody 6E10 (Senetek), and developed for exposure to ECL film. Quantification of retained, aggregated Aβ is performed by densitometry, calibrated against known amounts of the peptide.

Because metals, such as Zn++ and Cu+, trigger the pathologic aggregation of Aβ, an important causal factor in Alzheimers disease, we tested the ability of endogenous prophyrins to prevent Aβ aggregation using published methodology. We found that these endogenous porphyrins, are capable of dismantling aggregated Aβ and preventing the aggregation of monomeric Aβ. The effect of porphyrins on Aβ is likely mediated by their ability to chelate metals. In addition, we found that heme itself will displace metals from the aggregated Aβ and disaggregate the complex (Atamna, 2004). These results suggest that these endogenous porphyrins have biological roles. Endogenous porphyrins can be used directly, or their synthesis can be triggered in tissue by applying their precursors and/or cofactors, for therapeutic purposes including the treatment and prevention of disorders that involve Aβ aggregation and/or metal toxicity. Changes in the metabolism of porphyrins can also be used as markers to identify people with an elevated risk of developing Alzheimer's disease (AD) or to assess the clinical status of AD patients.

Example 2

Metal Chelation by Endogenous Porphyrins Affects Endogenous Metal Homeostasis and the Toxicity of Heavy Metals We studied the interaction between metals and porphyrin intermediates. We demonstrated that the porphyrin intermediates are capable of binding both toxic (Cd, Hg) and physiologic metals (Mn, Zn, and Cu). Results are shown in Tables 1A and 1B.

TABLE 1A

| Cpor(nm) | 370 | 500 | — | 538 | 560 | — | 608 |
|---|---|---|---|---|---|---|---|
| +Zn | 400 | Dis | — | Inc | Inc | 575a | Dis |
| +Cu | = | = | 525a | Dec | Dec | — | Dis |
| +Mn | = | = | | = | = | | = |

TABLE 1B

| Upor(nm) | 395 | — | 498 | — | 540 | 565 | — | 612 |
|---|---|---|---|---|---|---|---|---|
| +Zn | 405 | — | Dis | — | Inc | Dis | 575a | Dis |
| +Cu | Inc | — | Dis | 525a | Dis | Inc | — | Dis |
| +Mn | Inc | 460a | Dis | 545a | Dis | Dis | 575a | Dis |

Dis; peak disappeared. Inc; Peak increased. Dec; peak decreased. Upor; Uroporphyrin III. Cpor; Coproporphyrin III. (a)indicates new peak. = indicates no difference from the control (raw in bold).

Example 3

Porphyrins Inhibit β-Amyloid Accumulation in Alzheimer's Disease Transgenic Mice The affect of human porphyrin intermediates on Aβ aggregation in the APP25576 transgenic (Tg) mouse model of AD, is demonstrated using methodology adapted from Cherny et al, 2001 (below). In this Tg mouse model, the amyloid deposits are enriched with Zn and Fe, resembling amyloid deposits in AD. Tg mice are housed and fed according to standard animal care protocols. The choice of dose of human porphyrins (Cpor I, Cpor III, Upor I and Upor III) is based upon in vitro Aβ aggregation assays. Dosages of 50 mg/kg/d or less are evaluated over the course of 12 weeks.

The animals are examined daily by a blinded operator, and a measurement of each animal's general behavior in its cage is taken by observation based upon a subjective 5 point rating scale, where 5 is alert, grooming, normal withdrawal response upon handling, and no obvious motor abnormality; 4 is either distressed or lethargic, not grooming, lost withdrawal response upon handling, but no motor abnormality; 3 is periodic obvious motor abnormality (paresis, spinning, tremor, rigidity); 2 is persistent motor abnormality or cachexia; and 1 is moribund. The animals are also weighed at intervals. Equality of survival distributions is statistically tested by log-rank analysis. All statistical analyses use Systat 9.0 (SPSS, Inc.). At the completion of all studies, the animals are anesthetized, a blood sample obtained, cardiac-perfused with cold saline, and the brain and peripheral organs are removed. The left cerebral hemisphere is fixed in 4% paraformaldehyde, and the right hemisphere (without cerebellum) and remaining tissues are weighed and snap frozen in liquid nitrogen.

Snap-frozen tissues are thawed and homogenized in PBS (pH 7.4, 2 ml) and centrifuged at 100,000×g for 30 min. Aβ in the supernatants (soluble), the pellet, in an aliquot of homogenate (total), and in serum, is quantified by Western blot using WO2, an anti-Aβ monoclonal antibody that detects all forms of full-length Aβ, calibrated with known quantities of synthetic Aβ. APP is quantified by Western blot from the same samples using 22C11 (Boehringer), which detects both the transgene-expressed human APP as well as the endogenous mouse APP, and using recombinant APP standards. This antibody is directed to the amino terminus of APP and cannot differentiate between soluble and full-length APP; therefore, soluble and full-length APP levels are respectively measured from the supernatant and SDS—extracted pellet fractions of the cerebral homogenates after ultracentrifugation.

Histological sections of whole brain are prepared and the proportional surface area of amyloid plaques estimated by computer-assisted immunohistochemical quantification (using monoclonal antibody 1E8). Sections of the hippocampus are also stained with a monoclonal antibody against glial fibrillary acidic protein (DAKO) and the number of cells in the pyramidal layer staining positively per high-powered field (hpf) is determined (n=3 fields, n=3 sections). The operator remains blind to the porphyrin treatment status of the tissue. Data from the treated and untreated animal groups are analyzed by two-tailed t test.

Example 4

Porphyrin Administration to AD Patients

Methodology for this clinical trial is adapted from a protocol demonstrating effectiveness of the metal chelating agent, Clioquinol, in treatment of Alzheimer's Disease (Ritchie, 2003). Criteria for participation in the study includes informed consent; a diagnosis of probable AD by means of criteria of the National Institute of Neurological and Communicative Disorders and Stroke and the Alzheimer's Disease and Related Disorders Association; a cognitive subscale score on the Alzheimer's Disease Assessment Scale (ADAS-cog score) of 20 to 45; a Mini-Mental State Examination score of 10 to 24; and receipt of a 5- to 10-mg dose of donepezil for at least 6 months.

The study is a double-blind, placebo-controlled, parallel group randomized design. Thirty-six patients and their caregivers are recruited. The duration of the study is 36 weeks. An oral dosage of human porphyrin (Cpor I, Cpor III, Upor I or Upor III) is administered at 125 mg twice daily from weeks 0 to 12, 250 mg twice daily from weeks 13 to 24, and 375 mg twice daily from weeks 25 to 36.

Screening procedures consist of a medical history, physical examination, psychometric tests, nerve conduction tests, and visual evoked responses. Blood is collected for Apolipoprotein E allotyping and assays of metals and Aβ. All patients continue to receive donepezil and receive intramuscular cyanocobalamin (vitamin B12), 100 μg, every 4 weeks. Standard adverse event reporting is conducted. Visual evoked responses and results of nerve conduction studies and a full ophthalmic examination are obtained at screening, at week 16, and before the final trial visit.

The primary efficacy variable is change from the baseline score on the ADAS-cog at weeks 4, 12, 24, and 36. Plasma Aβ, zinc, and copper levels are all measured every 4 weeks. At weeks 12, 24, and 36, porphyrin blood levels are assayed by HPLC. For Aβ detection, ELISA plates are coated with monoclonal antibody (mAb) G210 (for $A\beta_{40}$) or mAb G211 (for $A\beta_{42}$) and washed, and biotinylated mAbWO2 is added. Bound antibody is detected with streptavidin-labeled Europium (PerkinElmer, Inc).

Evidence of efficacy is indicated by a significant difference in change from baseline between treatment arms. Analysis of variance is the principal method of evaluating statistical significance. Differences between groups on categorical measures are analysed using exact statistical methods. The baseline illness severity factor is created, as planned, by division of the sample into 2 groups at the median ADAS-cog score at baseline, yielding less severely and more severely affected groups (n=8 and n=8, respectively, in the porphyrin treatment arm; and n=7 and n=9, respectively, in the placebo arm).

Example 5

Porphyrin Therapy for Treatment of Mercury Toxicity

Two prolonged methylmercury-exposure studies are undertaken using protocols adapted from Pingree (2001). Study 1 evaluates the efficacy of human porphyrins (Cpor I, Cpor III, Upor I and Upor III) dosage on mercury clearance from brain and kidney. In this study, male Fischer-344 rats (200-225 g) are divided into two groups of 12 and 18 rats. The larger group is placed on a continuous regimen of drinking water containing 10 ppm methylmercury (II) hydroxide ($CH_3HgOH$, MMH) MMH, and the group of 12 is placed on deionized water ($dH_2O$) as controls. After 6 weeks, all rats are transferred to individual metabolism cages for 24-h urine collections. The animals that receive MMH for 6 weeks are divided randomly into 3 groups of 6 rats each. The first 2 groups of 6 animals receive single ip injections of porphyrin at either 100 mg/kg or 200 mg/kg, respectively, whereas the third group receives saline injections. Concurrently, the 12 $dH_2O$ control rats are divided into 3 groups of 4 each and given comparable injections of 100 or 200 mg/kg porphyrin or saline. Subsequently, all rats are returned to individual metabolism cages for post-treatment 24-h urine collections. All animals are then sacrificed, and tissues are collected for mercury assessments.

The second study (Study 2) is designed to assess the effect of consecutive porphyrin treatments on mercury clearance from brain, kidney, and blood of MMH-exposed rats. In this study, 30 rats are placed on a continuous regimen of drinking water containing 10 ppm MMH for 6 weeks. The prechelation concentrations of both $Hg^{2+}$ and $CH_3Hg^+$ in renal cortex are sufficient following 6 weeks of MMH exposure to permit evaluation of the efficacy of Porphyrin chelation in clearing both organic and inorganic mercury species from kidney, as well as from brain and blood.

To determine the effects of multiple Porphyrin treatments on tissue mercury levels, animals are given up to 3 porphyrin injections over a period of 3-7 days prior to sacrifice. For this study, the 30 MMH-exposed rats are divided into 2 groups of 18 and 12 animals, respectively. The first group of 18 rats receives a single ip injection of 100 mg/kg porphyrin, whereas the remaining 12 are given a saline injection, as controls. All 30 animals are then transferred to individual metabolism cages for 24-h urine collections. Rats are denied food but are freely provided $dH_2O$ during the urine collection period. Following urine collections, 6 animals from the porphyrin-treatment group and 4 rats from the control group are sacrificed, and brains, kidneys, and blood are retrieved for mercury analyses. Seventy-two hours after the first injection, the remaining 12 porphyrin-treated rats are given a second 100 mg/kg porphyrin injection, while the remaining 8 saline-treated rats are given a second saline injection. After 24 h, 6 of the porphyrin-treated rats and 4 of the control rats are sacrificed and tissues collected. Seventy-two h after the second injection the remaining animals are given a third porphyrin or saline treatment. Twenty-four h after the third injection all remaining rats are sacrificed and tissues collected. Between porphyrin treatments, animals are held in metabolism cages without food but with dH2O for 24-h urine collections and then returned to their hanging cages and permitted food and water for 48 hours. In all studies, animals are anesthetized by carbon dioxide (CO2) and then sacrificed by decapitation. Blood is obtained by cardiac puncture into heparinized tubes prior to sacrifice. Brains and kidneys are harvested surgically immediately following sacrifice. All tissues are preserved at $-80°$ C. until mercury analysis.

For urine collection, animals are placed in hanging metabolism cages for 24 h with free access to drinking water (containing either MMH or dH2O) but not food. The metabolism cages are fitted with metal funnels attached to the bottom with a plastic ping-pong ball placed at the hole of the funnel to allow urine but not feces to pass through. Aluminum foil-covered, polypropylene 125-ml volumetric flasks are placed under the funnels to collect the urine without allowing evaporation. At the end of 24 h the urine volume is measured. The urine is then acidified with a drop of 6 N HCl and frozen at $-20°$ C. until mercury analysis.

Urinary mercury is measured using a digestion method. 2.5 ml of HCl and 2-ml bromate/bromide solution is added to a 2.5-ml urine sample and allowed to sit overnight in a 20-ml glass scillation vial. Hydroxylammonium chloride (20%) is then added to decolorize the sample and to stop the digestion process. The fully digested sample is transferred to a 50-ml borosilicate glass volumetric flask, and distilled water is added to a total volume of 50 ml. The total (organic and inorganic) mercury content of the sample is then analyzed by cold vapor atomic fluorescence spectroscopy (CVAFS) using a PSA Merlin Mercury Analysis System (Questron Corp., Mercerville, N.J.). For inorganic mercury ($Hg^{2+}$) determinations, a 0.5-ml sample of urine is digested overnight in 2 ml of $HNO_3$. The sample is then diluted to a volume of 20 ml with $dH_2O$, and the total $Hg^{2+}$ content is measured using CVAFS. The organic mercury content of the sample is determined by the difference in the total and inorganic mercury values.

The total and inorganic mercury concentrations in kidney and brain tissues are analyzed by CVAFS following digestion and preparation of tissues. The organic mercury content of tissue samples is again determined by the difference in the total and inorganic mercury concentrations.

Total and organic mercury concentrations in blood samples are directly measured by ethylation-GC-CVAFS after alkaline digestion-solvent extraction. Inorganic mercury is calculated as the difference between total and organic mercury.

For each these procedures, validation of $Hg^{2+}$ and $CH_3Hg^+$ analysis is confirmed by concomitant measurement of control urine or tissue samples containing a range of known concentrations of $Hg^{2+}$, $CH_3Hg^+$ or total mercury ($Hg^{2+}+CH_3Hg^+$) derived from standard reference materials. Data are presented as means±standard error of the mean (SEM). Statistical analyses are conducted using Student's t-test with 1-tailed distribution. p values less than 0.05 are considered significant.

Example 6

δ-Aminolevulinic Acid Treatment of Mercury Toxicity

To evaluate the efficacy of δ-aminolevulinic acid and Vitamin B6 therapies on mercury clearance from brain and kidney, the procedures of Example 5 are followed, except that up to 6 injections of δ-aminolevulinic acid and/or vitamin B6 are given over a period of 14 days prior to sacrifice.

Example 7

Vitamin B6 Treatment for Aluminum Toxicity

Elderly patients demonstrating one or more symptoms of Alzheimer's disease are tested for increased serum aluminum (>50 μg/l). Patients demonstrating increased serum aluminum are identified as predisposed to a polycarboxylated porphyrin-binding metal toxicity, and are prescribed 50 mg daily vitamin B6 to increase endogenous uroporphyrin and coproporphyrin production. Follow up testing showing a reduction in serum aluminum and improved cognitive abilities is indicative of a resultant increase in endogenous polycarboxylated porphyrins.

The foregoing examples and detailed description are offered by way of illustration and not by way of limitation. All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

REFERENCES

Atamna and Frey, "A role for heme in Alzheimer's disease: Heme binds amyloid β and has altered metabolism" PNAS (2004) 101:11153-11158.
Atamna et al., "Heme deficiency may be a factor in the mitochondrial and neuronal decay of aging" Proc Natl Acad Sci USA. (2002) 99:14807-14812.

Beer at al., "Pyrrole-based metallo-macrocycles and cryptands" Dalton Transactions (2003) 4:603-611.

Bowers et al., "Quantitative determination of porphyrins in rat and human urine and evaluation of urinary porphyrin profiles during mercury and lead exposures." J Lab Clin Med. (1992) 120:272-81.

Brown et al, "The present and future role of photodynamic therapy in cancer treatment." Lancet Oncol. (2004) 5:497-508.

Caughey, W S and Caughey, B "Inhibitors of Amyloid Formation" (2003) U.S. Pat. No. 6,632,808.

Caughey et al, "Inhibition of protease-resistant prion protein formation by porphyrins and phthalocyanines", Proc Natl Acad Sci USA. (1998) 95:12117-12122.

Cherny et al, "Treatment with a Copper-Zinc Chelator Markedly and Rapidly Inhibits β-Amyloid Accumulation in Alzheimer's Disease Transgenic Mice." Neuron (2001) 30: 665-676.

Daniell et al., "Environmental Chemical Exposures and Disturbances of Heme Synthesis" Environ Health Perspect (1997) 105 (Suppl 1):37-53.

El-Agnaf et al "Alpha-synuclein implicated in Parkinson's disease is present in extracellular biological fluids, including human plasma." FASEB J. (2003) 17:1945-7.

Gold et al, "δ-aminolevulinic acid photodynamic therapy: where we have been and where we are going." Dermatol Surg. (2004) 30:1077-83.

Grandchamp et al. "Formation and disposition of newly synthesized heme in adult rat hepatocytes in primary culture." J Biol. Chem. 1981 Nov. 25; 256(22):11677-83.

Howlett et al. "Hemin and related porphyrins inhibit β-amyloid aggregation" FEBS Letters 417 (1997) 249-251.

Ingi et al, "The regulation of heme turnover and carbon monoxide biosynthesis in cultured primary rat olfactory receptor neurons." J. Neurosci. (1996) 16:5621-8.

Lee et al, "Visualization of beta-amyloid plaques in a transgenic mouse model of Alzheimer's disease using MR microscopy without contrast reagents." Magn Reson Med. (2004) 52:538-44.

Lerch et al. "Focal Decline of Cortical Thickness in Alzheimer's Disease Identified by Computational Neuroanatomy." Cereb Cortex. (2004) November 10; [Epub ahead of print]

Mehra R, Juneja M, "Variation of concentration of heavy metals, calcium and magnesium with sex as determined by atomic absorption spectrophotometry." Indian J Environ Health. (2003) 45:317-24.

Miller et al, "Homocysteine, vitamin B6, and vascular disease in AD patients." Neurology. (2002) 58:1471-5.

Miyajima et al, "Aceruloplasminemia, an inherited disorder of iron metabolism." Biometals (2003) 16:205-13.

Nakayama et al, "Spontaneous Porphyria of the Long-Evans Cinnamon Rat: An Animal Model of Wilson's Disease" Arch Biochem Biophys. (2000) 375:240-50.

Pingree et al, "Effects of 2,3-dimercapto-1-propanesulfonic acid (DMPS) on tissue and urine mercury levels following prolonged methylmercury exposure in rats." Toxicol Sci. (2001) 61:224-33.

Ponka, "Cell Biology of Heme" Am J Med Sci. (1999) 318: 241-56.

Priola et al, "Porphyrin and phthalocyanine antiscrapie compounds", Science (2000) 287:1503-1506.

Ritchie et al, "Metal-protein attenuation with iodochlorhydroxyquin (clioquinol) targeting Aβ Amyloid deposition and toxicity in Alzheimer Disease" Arch Neurol (2003) 60:1685-1691.

Ritchie et al, "Metal-protein attenuating compounds and Alzheimer's disease." Expert Opin Investig Drugs. (2004) 13:1585-92.

Uversky et al, "Metal-triggered structural transformations, aggregation, and fibrillation of human alpha-synuclein. A possible molecular NK between Parkinson's disease and heavy metal exposure." J Biol. Chem. (2001) 276:44284-96.

Whetsell et al., "Studies on porphyrin-heme biosynthesis in organotypic cultures of chick dorsal root ganglion. I. Observations on neuronal and non-neuronal elements." J Neuropathol Exp Neurol. (1978) 37:497-507.

Woods J S. "Studies on the rate-limiting role of delta-aminolevulinic acid synthetase in heme biosynthesis in fetal rat liver." In Porphyrins in Human Diseases. M Doss, ed. Basel: S. Karger Publishing Company, 1976; 86-97.

What is claimed is:

1. A method for increasing an amount of an endogenous porphyrin in an individual in need thereof, the method comprising the steps of:
    (a) determining that the individual has or is predisposed to amyloid-β aggregation, and has or is predisposed to an associated endogenous porphyrin underproduction; and
    (b) increasing the level of the porphyrin in the individual by orally administering the porphyrin without bound metal to obtain a resultant increase in the amount of the porphyrin in the individual, relative to the amount of the porphyrin in the individual prior to administering the porphyrin,
    wherein the porphyrin is uroporphyrin I, uroporphyrin III, coproporphyrin I, or coproporphyrin III.

2. The method of claim 1 wherein the porphyrin is uroporphyrin I.

3. The method of claim 1 wherein the porphyrin is uroporphyrin III.

4. The method of claim 1 wherein the porphyrin is coproporphyrin I.

5. The method of claim 1 wherein the porphyrin is coproporphyrin III.

6. A method for increasing an amount of an endogenous porphyrin in an individual in need thereof, the method comprising the steps of:
    (a) determining that the individual has or is predisposed to amyloid-β aggregation, and has or is predisposed to an associated endogenous porphyrin underproduction; and
    (b) increasing the level of the porphyrin in the individual by orally administering a precursor of the porphyrin to obtain a resultant increase in the amount of the porphyrin in the individual, relative to the amount of the porphyrin in the individual prior to administering the porphyrin,
    wherein the porphyrin is uroporphyrin I, uroporphyrin III, coproporphyrin I, or coproporphyrin III, and wherein the precursor is δ-aminolevulinic acid, porphobilinogen, or hydroxymethylbilane.

7. The method of claim 6 wherein the precursor is δ-aminolevulinic acid.

8. The method of claim 6 wherein the precursor is porphobilinogen.

9. The method of claim 6 wherein the precursor is hydroxymethylbilane.

10. A method for increasing an amount of an endogenous porphyrin in an individual in need thereof, the method comprising the steps of:

(a) determining that the individual has or is predisposed to amyloid-β aggregation, and has or is predisposed to an associated endogenous porphyrin underproduction; and (b) increasing the level of the porphyrin in the individual by orally administering a cofactor in the biosynthetic pathway of the porphyrin to obtain a resultant increase in the amount of the porphyrin in the individual, relative to the amount of the porphyrin in the individual prior to administering the porphyrin, wherein the porphyrin is uroporphyrin I, uroporphyrin III, coproporphyrin I, or coproporphyrin III, and wherein the cofactor is pantothenic acid (vitamin B5), pyridoxal phosphate (vitamin B6), zinc, or biotin (vitamin H).

11. The method of claim 10 wherein the cofactor is pantothenic acid (vitamin B5).

12. The method of claim 10 wherein the cofactor is pyridoxal phosphate (vitamin B6).

13. The method of claim 10 wherein the cofactor is zinc.

14. The method of claim 10 wherein the cofactor is biotin (vitamin H).

15. The method of claim 1, further comprising the step of:

(c) detecting the resultant increase in the amount of the porphyrin in the individual, relative to the amount of the porphyrin in the individual prior to administering the porphyrin.

16. The method of claim 6, further comprising the step of:

(c) detecting the resultant increase in the amount of the porphyrin in the individual, relative to the amount of the porphyrin in the individual prior to administering the porphyrin.

17. The method of claim 10, further comprising the step of:

(c) detecting the resultant increase in the amount of the porphyrin in the individual, relative to the amount of the porphyrin in the individual prior to administering the porphyrin.

18. The method of claim 1, wherein the increasing step further comprises orally administering a precursor of the porphyrin, wherein the precursor is δ-aminolevulinic acid, porphobilinogen, or hydroxymethylbilane.

19. The method of claim 1, wherein the increasing step further comprises orally administering a cofactor in the biosynthetic pathway of the porphyrin, wherein the cofactor is pantothenic acid (vitamin B5), pyridoxal phosphate (vitamin B6), zinc, or biotin (vitamin H).

20. The method of claim 1, wherein the increasing step further comprises orally administering a precursor of the porphyrin, wherein the precursor is δ-aminolevulinic acid, porphobilinogen, or hydroxymethylbilane, and a cofactor in the biosynthetic pathway of the porphyrin, wherein the cofactor is pantothenic acid (vitamin B5), pyridoxal phosphate (vitamin B6), zinc, or biotin (vitamin H).

* * * * *